United States Patent [19]  
Schurter et al.

[11] Patent Number: 4,594,097  
[45] Date of Patent: Jun. 10, 1986

[54] N-PHENYLSULFONYL-N'-TRIAZINYLUREAS

[75] Inventors: Rolf Schurter, Binningen; Werner Föry, Basel; Willy Meyer, Riehen, all of Switzerland

[73] Assignee: Ciba-Geigy Corporation, Ardsley, N.Y.

[21] Appl. No.: 745,749

[22] Filed: Jun. 17, 1985

Related U.S. Application Data

[62] Division of Ser. No. 496,326, May 19, 1983, Pat. No. 4,537,618.

[30] Foreign Application Priority Data

May 26, 1982 [CH] Switzerland ............... 3232/82

[51] Int. Cl.⁴ ............... C07D 251/50; C07D 251/52; C07D 401/12; A01N 43/70
[52] U.S. Cl. ............... 71/93; 71/92; 71/90; 544/211; 544/206; 544/208; 544/197
[58] Field of Search ............... 544/211, 206, 208, 197; 71/93, 90

[56] References Cited

U.S. PATENT DOCUMENTS 4,368,069 1/1983 Chen et al. ............... 71/93  
4,419,121 12/1983 Meyer et al. ............... 71/92  
4,425,154 1/1983 Meyer et al. ............... 71/92

FOREIGN PATENT DOCUMENTS 44210 1/1982 European Pat. Off. .

OTHER PUBLICATIONS

Hayman et al., C.A. 63, (1965), col. 520h–col. 521a.

Primary Examiner—John M. Ford  
Attorney, Agent, or Firm—Edward McC. Roberts; Irving M. Fishman

[57] ABSTRACT

N-Phenylsulfonyl-N'-pyrimidinylureas and N-phenylsulfonyl-N'-triazinylureas of the general formula I

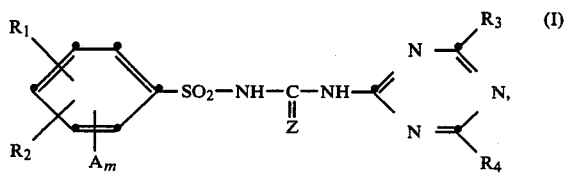

wherein
A is a radical of the formula —C≡C—R,
m is 1 or 2,
Z is oxygen or sulfur,
R is hydrogen; unsubstituted or substituted, branched or unbranched $C_1$–$C_9$alkyl; unsubstituted or substituted $C_3$–$C_9$cycloalkyl; unsubstituted or substituted phenyl; or an unsubstituted or substituted 5- or 6-membered aromatic heterocyclic ring,
$R_1$ is hydrogen, halogen, $C_1$–$C_5$alkyl, $C_2$–$C_5$alkenyl or a radical —Y—$R_5$,
$R_2$ is hydrogen, halogen, $C_1$–$C_5$alkyl, $C_2$–$C_5$alkenyl, $C_1$–$C_4$haloalkyl, or a radical —Y—$R_5$, —COOR$_6$, —NO$_2$ or —CO—NR$_7$—R$_8$,
$R_3$ and $R_4$, each independently of the other, are hydrogen, $C_1$–$C_4$alkyl, $C_1$–$C_4$alkoxy, $C_1$–$C_4$alkylthio, $C_1$–$C_4$haloalkyl, $C_1$–$C_4$haloalkoxy, $C_1$–$C_4$haloalkylthio, halogen, $C_2$–$C_5$alkoxyalkyl, —NR$_9$R$_{10}$ or —O—CH$_2$—CH$_2$—NR$_9$R$_{10}$,
$R_5$ and $R_6$, each independently of the other, are $C_1$–$C_5$alkyl, $C_2$–$C_5$alkenyl or $C_2$–$C_6$alkynyl, $C_1$–$C_5$haloalkyl, $C_2$–$C_5$haloalkenyl or $C_2$–$C_6$alkoxyalkyl,
$R_7$ and $R_8$, each independently of the other, are hydrogen, $C_1$–$C_5$alkyl, $C_2$–$C_5$alkenyl or $C_2$–$C_6$alkynyl,
$R_9$ is hydrogen, methyl or ethyl,
$R_{10}$ is hydrogen, $C_1$–$C_4$alkyl, $C_1$–$C_4$alkoxy, methoxymethyl, cyanomethyl, cyanoethyl, $C_3$–$C_5$alkenyl or $C_3$–$C_6$alkynyl, and
Y is oxygen, sulfur, a sulfinyl or sulfonyl bridge and the salts of these compounds with amines, alkali metal bases or alkaline earth metal bases or with quaternary ammonium bases, have good preemergence and postemergence selective herbicidal and growth regulating properties.

14 Claims, No Drawings

N-PHENYLSULFONYL-N'-TRIAZINYLUREAS

This is a divisional of application Ser. No. 496,326 filed on May 19, 1983, now U.S. Pat. No. 4,537,618.

The present invention relates to novel N-phenylsulfonyl-N'-pyrimidinylureas and N-phenylsulfonyl-N'-triazinylureas having herbicidal and plant growth-regulating properties, to the production thereof, to compositions containing them, and to the use thereof for controlling weeds, in particular selectively, in crops of useful plants, or for regulating and inhibiting plant growth. The invention also relates to novel phenylsulfonamides prepared as intermediates.

The N-phenylsulfonyl-N'-pyrimidinylureas and N-phenylsulfonyl-N'-triazinylureas of this invention, and the salts thereof, have the general formula I

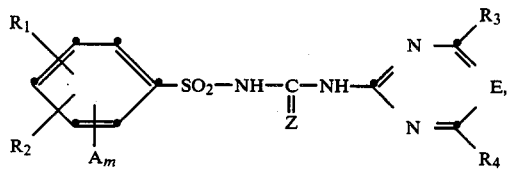

wherein
A is a radical of the formula —C≡C—R,
m is 1 or 2,
E is the methine group or nitrogen,
Z is oxygen or sulfur,
R is hydrogen; branched or unbranched $C_1$-$C_9$alkyl which is unsubstituted or substituted by halogen, hydroxyl, $C_1$-$C_4$alkoxy, $C_1$-$C_4$alkylthio, $C_1$-$C_4$haloalkoxy, $C_3$-$C_9$cycloalkyl, cyano, —$COOR_6$, —$CONR_7R_8$ or by phenyl which is in turn unsubstituted or substituted by halogen, $C_1$-$C_4$alkyl, $C_1$-$C_4$alkoxy, nitro, cyano or trifluoromethyl; or is $C_3$-$C_9$cycloalkyl which is unsubstituted or substituted by halogen, hydroxyl, $C_1$-$C_4$alkyl, $C_1$-$C_4$alkoxy, $C_1$-$C_4$alkylthio, cyano, —$COOR_6$, —$CONR_7R_8$; or is phenyl or phenyl substituted by halogen, nitro, cyano, $C_1$-$C_4$alkyl, $C_1$-$C_4$alkoxy, $C_1$-$C_4$alkylthio, trifluoromethyl, —$COOR_6$ or —$CONR_7R_8$; or is a 5- or 6-membered aromatic heterocyclic ring which is unsubstituted or substituted by halogen, $C_1$-$C_4$alkyl, $C_1$-$C_4$alkoxy, —$COOR_6$ or —$CONR_7R_8$,
$R_1$ is hydrogen, halogen, $C_1$-$C_5$alkyl, $C_2$-$C_5$alkenyl or a radical —Y—$R_5$,
$R_2$ is hydrogen, halogen, $C_1$-$C_5$alkyl, $C_2$-$C_5$alkenyl, $C_1$-$C_4$haloalkyl, or a radical —Y—$R_5$, —$COOR_6$, —$NO_2$ or —CO—$NR_7$—$R_8$,
$R_3$ and $R_4$, each independently of the other, are hydrogen, $C_1$-$C_4$alkyl, $C_1$-$C_4$alkoxy, $C_1$-$C_4$alkylthio, $C_1$-$C_4$haloalkyl, $C_1$-$C_4$haloalkoxy, $C_1$-$C_4$haloalkylthio, halogen, $C_2$-$C_5$alkoxyalkyl, —$NR_9R_{10}$ or —O—$CH_2$—$CH_2$—$NR_9R_{10}$,
$R_5$ and $R_6$, each independently of the other, are $C_1$-$C_5$alkyl, $C_2$-$C_5$alkenyl or $C_2$-$C_6$alkynyl, $C_1$-$C_5$haloalkyl, $C_2$-$C_5$haloalkenyl or $C_2$-$C_6$alkoxyalkyl,
$R_7$ and $R_8$, each independently of the other, are hydrogen, $C_1$-$C_5$alkyl, $C_2$-$C_5$alkenyl or $C_2$-$C_6$alkynyl,
$R_9$ is hydrogen, methyl or ethyl,
$R_{10}$ is hydrogen, $C_1$-$C_4$alkyl, $C_1$-$C_4$alkoxy, methoxymethyl, cyanomethyl, cyanoethyl, $C_3$-$C_5$alkenyl or $C_3$-$C_6$alkynyl, and
Y is oxygen, sulfur, a sulfinyl or sulfonyl bridge.

Herbicidally active ureas, triazines and pyrimidines are generally known in the art. Arysulfamoyl-heterocyclyl-aminocarbamoyl compounds with herbicidal and plant growth-regulating action are described e.g. in Netherlands patent specification No. 121 788 or in European patent application No. 44 210.

In the above definitions, alkyl denotes straight-chain or branched alkyl, e.g. methyl, ethyl, n-propyl, isopropyl, the four butyl isomers, n-amyl, isoamyl, 2-amyl, 3-amyl, n-hexyl or isohexyl, or the different heptyl, octyl or nonyl isomers.

Alkoxy denotes methoxy, ethoxy, n-propoxy, isopropoxy and the four butoxy isomers, with methoxy, ethoxy or isopropoxy being preferred.

Alkylthio is e.g. methylthio, ethylthio, n-propylthio, isopropylthio and n-butylthio, with methylthio and ethylthio being preferred.

Alkenyl radicals are e.g. vinyl, allyl, isoprenyl, propen-1-yl, buten-1-yl, buten-2-yl, buten-3-yl, isobuten-1-yl, isobuten-2-yl, penten-1-yl, penten-2-yl, penten-3-yl and penten-4-yl, with vinyl, allyl and penten-4-yl being preferred.

Halogen in the above definitions, as well as moiety of haloalkyl, haloalkoxy and haloalkylthio, is fluorine, chlorine and bromine, with fluorine and chlorine being preferred.

Alkynyl radicals in the above definitions are generally propargyl, butyn-2-yl, butyn-3-yl, as well as pentynyl or hexynyl isomers. Preferably, however, alkynyl is propargyl or butyn-2- or -3-yl.

Aromatic heterocyclic rings which may be a constituent of the substituent A are e.g.: furan, thiophene, pyrrole, pyrazole, triazole, pyridine, pyrimidine, pyridazine, triazine, thiazole, oxazole, thiadiazole or oxadiazole. Furan, thiophene and pyridine are preferred. These aromatic heterocyclic rings are most preferred when they are linked in the 2-position to the ethynyl bridge.

The invention also comprises the salts which the compounds of formula I are able to form with amines, alkali metal bases and alkaline earth metal bases, or with quaternary ammonium bases.

Preferred salt-forming alkali metal hydroxides and alkaline earth metal hydroxides are the hydroxides of lithium, sodium, potassium, magnesium or calcium, most preferably those of sodium or potassium.

Examples of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, diisopropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine and diethanolamine being most preferred.

Examples of quaternary ammonium bases are, in general, the cations of haloammonium salts, e.g. the tetramethylammonium cation, the trimethylbenzylammonium cation, the triethylbenzylammonium cation, the tetraethylammonium cation, the trimethylethylammonium cation, and also the ammonium cation.

Preferred compounds of the formula I are those in which
(a) Z is oxygen,
(b) $R_3$ and $R_4$ together contain not more than 4 carbon atoms, and
(c) m is 1.

Preferred compounds of group (c) are those in which the radical A is in the 2- or 3-position to the sulfonyl group.

A particularly preferred group of compounds of the formula I comprises those compounds in which only one radical A is in the 2- or 3-position to the sulfonyl group, Z is oxygen, and $R_3$ and $R_4$ together contain not more than 4 carbon atoms.

Preferred compounds belonging to this group are those in which $R_1$ is hydrogen and $R_2$ is in the 5- or 6-position to the sulfonyl group. Among these compounds, those compounds are in turn preferred in which $R_2$ is hydrogen, halogen, $C_1$-$C_4$alkoxy, $C_1$-$C_4$haloalkoxy, nitro, $C_1$-$C_4$alkyl, $C_1$-$C_4$haloalkyl or —$COOR_6$.

Further preferred compounds within this last mentioned group are those compounds in which $R_2$ is hydrogen, chlorine, fluorine, —$COOR_6$, nitro, methyl, trifluoromethyl, $C_1$-$C_4$haloalkoxy or $C_1$-$C_4$alkoxy, and each of $R_3$ and $R_4$ is hydrogen, $C_1$-$C_4$alkyl, $C_1$-$C_4$alkoxy, $C_1$-$C_4$alkylthio, dialkylamino, $C_1$-$C_3$haloalkoxy, halogen or alkoxyalkyl, whilst $R_3$ and $R_4$ together contain not more than 1 to 4 carbon atoms.

Among the individually preferred subgroups of compounds of formula I, those groups always merit particular preference in which R is hydrogen or branched or unbranched $C_1$-$C_4$alkyl which is unsubstituted or substituted by halogen, hydroxyl, methoxy, methylthio, $C_1$-$C_4$haloalkoxy, cyclopropyl, cyano or methoxycarbonyl, or is phenyl, pyridyl, thienyl or furyl.

A most particularly preferred subgroup comprises those compounds of formula I, wherein $R_1$ is hydrogen, $R_2$ is hydrogen, chlorine, fluorine, nitro, methyl, trifluoromethyl, $C_1$-$C_4$alkoxy, $C_1$-$C_4$haloalkyl or $C_1$-$C_4$alkoxycarbonyl which is in the 6-position, m is 1, and each of $R_3$ and $R_4$ is $C_1$-$C_4$alkyl, $C_1$-$C_4$alkoxy, methylthio, $C_1$-$C_2$haloalkyl, halogen or alkoxyalkyl, whilst $R_3$ and $R_4$ together contain not more than 4 carbon atoms, R is hydrogen or unbranched or branched $C_1$-$C_4$alkyl which is unsubstituted or substituted by halogen, hydroxyl, methoxy, methylthio, $C_1$-$C_4$haloalkoxy, cyclopropyl, cyano or methoxycarbonyl, or is phenyl, pyridyl, thienyl or furyl.

Preferred individual compounds are:
N-[2-(propyn-1-yl)-phenylsulfonyl]-N'-(4,6-dimethoxypyrimidin-2-yl)urea,
N-[2-(propyn-1-yl)-phenylsulfonyl]-N'-(4-methoxy-6-methylpyrimidin-2-yl)urea,
N-[2-(propyn-1-yl)-phenylsulfonyl]-N'-(4,6-dimethylpyrimidin-2-yl)urea,
N-[2-(2-phenylethynyl)-phenylsulfonyl]-N'-(4,6-dimethoxypyrimidin-2-yl)urea,
N-[2-(propyn-1-yl)-phenylsulfonyl]-N'-(4-methoxy-6-methyl-1,3,5-triazin-2-yl)urea and
N-[2-(3-hydroxy-3'-methylbutyn-1'-yl)-phenylsulfonyl]-N'-(4,6-dimethoxypyrimidin-2-yl)urea.

The process for obtaining the compounds of formula I is carried out in an inert organic solvent.

In a first process, the compounds of the formula I are obtained by reacting a phenylsulfonamide of the formula II

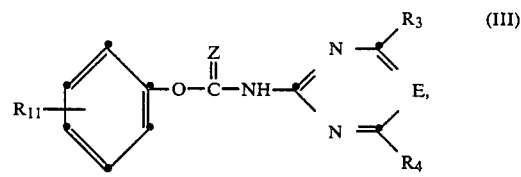

wherein A, $R_1$, $R_2$ and m are as defined for formula I, with a N-pyrimidinylcarbamate or N-triazinylcarbamate of the formula III

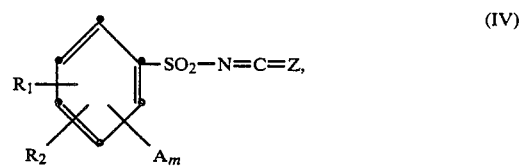

wherein E, $R_3$, $R_4$ and Z are as defined for formula I, and $R_{11}$ is hydrogen, halogen, $C_1$-$C_4$alkyl, $C_1$-$C_4$alkoxy, nitro, cyano or trifluoromethyl, in the presence of a base.

In a second process, compounds of formula I are obtained by reacting a phenylsulfonylisocyanate or phenylsulfonylisothiocyanate of the formula IV

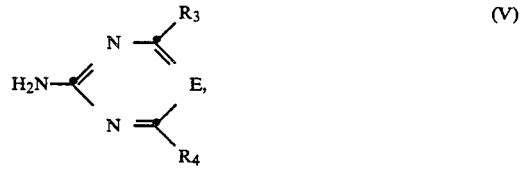

wherein A, $R_1$, $R_2$, m and Z are as defined for formula I, with an amine of the formula V

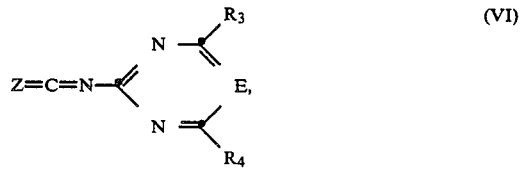

wherein E, $R_3$ and $R_4$ are as defined for formula I, in the presence of a base.

In a further process, the compounds of formula I are obtained by reacting a sulfonamide of the formula II above with an isocyanate or isothiocyanate of the formula VI

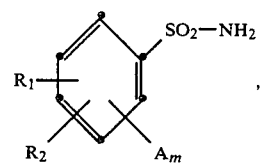

wherein E, $R_3$, $R_4$ and Z are as defined for formula I, optionally in the presence of a base.

Finally, the compounds of formula I can also be obtained by reacting a N-phenylsulfonylcarbamate of the formula VII

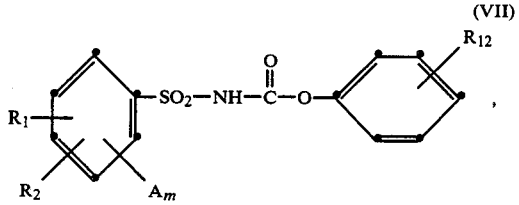

wherein A, $R_1$, $R_2$ and m are as defined for formula I, and $R_{12}$ is hydrogen, halogen, $C_1$-$C_4$alkyl, $C_1$-$C_4$alkoxy, nitro, cyano or trifluoromethyl, with an amine of the formula V above.

If desired, the ureas of formula I can be converted into salts with amines, alkali metal hydroxides or alkaline earth metal hydroxides, or with quaternary ammonium bases. This conversion is carried out e.g. by reacting the compounds of formula I with the equimolar amount of a base and removing the solvent by evaporation.

The starting materials of the formulae II, IV and VII are novel and can be prepared by the following methods.

The novel sulfonamides of formula II used as intermediates are obtained from the corresponding halophenylsulfonamides (IX) by reaction with acetylene compounds in accordance with the following reaction scheme A. Similar methods of obtaining ethynyl compounds are described in European patent application No. 41 476.

an aromatic radical. Hal is chlorine, but bromine and iodine are preferred. Alkyl is a $C_1$-$C_4$alkyl radical.

Method α is a process which makes it possible, using metal catalysts, to bond halogenated radicals, as in formula IX or XI, to terminal acetylene groups, as in formulae VIII, X and XIII, under mild reaction conditions, in the presence of an acid acceptor. Reactions of this kind are described in the following publications: K. Sonogashire, Y. Tohda and N. Hagihara, Tetrahedron Lett., 50, 4467 (1975); L. Cassar, J. Organomet. Chem., 93, 253 (1975), and H. A. Dieck and F. R. Heck, J. Organomet. Chem., 93, 259 (1975).

This reaction conveniently takes place in organic solvents which are inert to the reactants. Suitable solvents of this kind are many protic and aprotic solvents, e.g. alkanols, ketones, ethers, hydrocarbons, halogenated hydrocarbons, aromatic solvents such as methanol, ethanol, isopropanol, cyclohexanone, acetone, methyl ethyl ketone, diethyl ether, dimethyl ether, tetrahydrofuran, dioxan, cyclohexane, pentane, hexane, heptane, octane, methylene chloride, chloroform, carbon tetrachloride, benzene, toluene or xylene, or also e.g. dimethylformamide, dimethylsulfoxide, acetonitrile or tertiary amines such as triethylamine.

As dehydrohalogenation occurs during the reaction, a base can be used as acid acceptor. Suitable bases are e.g. strong inorganic bases such as KOH or NaOH, and also organic bases, such as triethylamine, diethylamine, pyridine, alcoholates etc. The amount of base employed in the reaction is from 1 to 5 equivalents. As metal catalysts it is preferred to use palladium salts or com- Scheme A:

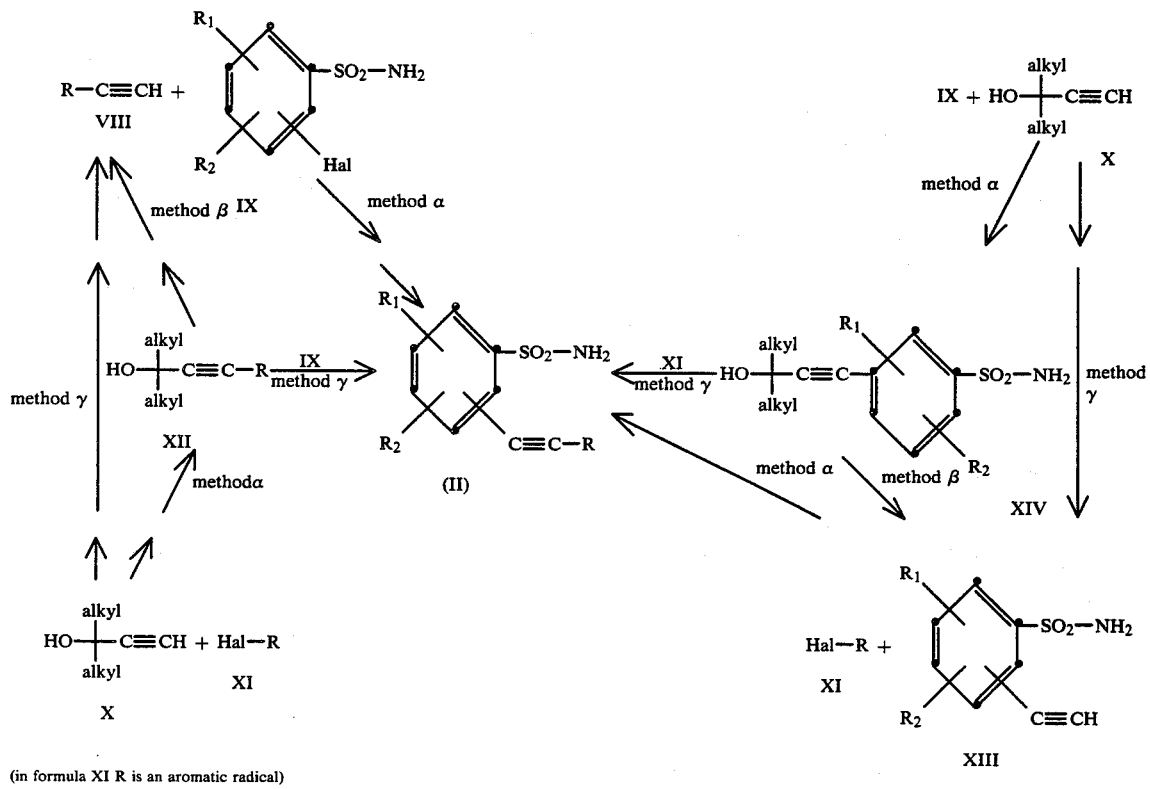

(in formula XI R is an aromatic radical)

In scheme A, the symbols R, $R_1$ and $R_2$ are as defined for formula I, with the proviso that R in formula XI is plexes, in particular palladium chloride ($PdCl_2$), palladium acetate ($Pd(OCOCH_3)_2$), or the palladium dichlorobis(triphenylphosphine) complex PdCl$_2$[P(C$_6$H$_5$)$_3$]$_2$, usually with the addition of a copper(I) salt, especially of copper(I) iodide. The catalysts are employed by themselves or applied to a carrier, e.g. ground charcoal, alumina etc.

The reaction temperatures are generally in the range from 0° C. to 200° C., but are in the main between room temperature and the boiling point of the reaction mixture. The reaction times are generally from ½ hour to 48 hours.

Method β makes it possible, in the presence of a strong base such as NaOH, KOH or an alcoholate, to liberate the acetylene from a tertiary ethynyl alcohol, as in formulae X, XII and XIV, which may be unterstood as a protected terminal acetylene group, with removal of the keto protective group, as in formulae VIII and XIII. The ketones obtained as by-products can be removed from the reaction mixture by distillation during the reaction. Reactions of this kind are described in German Offenlegungsschrift No. 2 905 507 and U.S. Pat. No. 4,128,588.

It is advantageous to conduct this reaction in an inert organic solvent such as an alcohol, an ether, a ketone, a hydrocarbon, a halogenated hydrocarbon, an aromatic solvent, or also in dimethylformamide, dimethylsulfoxide or acetonitrile. Examples of such solvents are: methanol, ethanol, isopropanol, dimethyl ether, diethyl ether, tetrahydrofuran, dioxan, acetone, methyl ethyl ketone, cyclohexanone, cyclohexane, benzene, toluene, xylene, methylene chloride, chloroform or carbon tetrachloride.

The reaction temperature in this case too is also preferably in the range between room temperature and the boiling point of the solvent. The reaction time is generally from ½ hour to 12 hours.

Method γ is a combination of methods α and β, except that the acetylene to be reacted by method α is prepared in situ by treating a protected acetylene of the formula X, XII and XIV with a strong base. The reaction conditions are identical with those of method α. However, the addition of a strong base such as NaOH, KOH or the alkali metal salt of an alcohol, is mandatory.

In accordance with the process outlined above, the compounds of formula II are obtained elither by reacting an ethynyl compound of the formula VIII

R—C≡CH (VIII)

with a halophenylsulfonamide of the formula IX

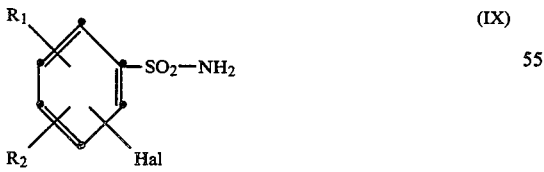
(IX)

in the presence of an acid acceptor and a metal catalyst and, if desired, in an inert gas atmosphere, or by reacting an aromatic halide of the formula XI

Hal—R' (XI)

under the same reaction conditions, with an ethynyl phenylsulfonamide of the formula XIII

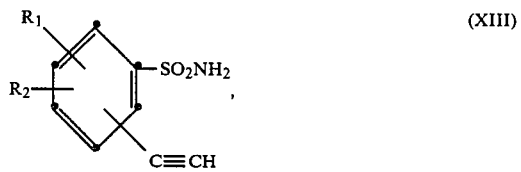
(XIII)

in which formulae above R$_1$ and R$_2$ are as defined for formula I, R' is an aromatic radical and Hal is bromine or iodine.

In a further process, the compounds of formula II are obtained by reacting an aromatic halide of the formula XI Hal—R' (XI)

with a propargyl alcohol of the formula X

(X)

in the presence of an acid acceptor and a metal catalyst and, if desired, under an inert gas atmosphere, and reacting the resultant ethynyl compound of the formula XII

(XII)

with a halophenylsulfonamide of the formula IX

(IX)

in the presence of a strong base and a metal catalyst, if desired under an inert gas atmosphere, or by reacting the halophenylsulfonamide of the formula IX, under the above reaction conditions, first with the propargyl alcohol of the formula X, and then reacting the ethynyl compound of the formula XIV

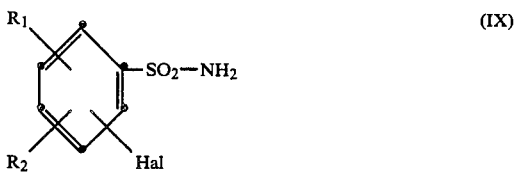
(XIV)

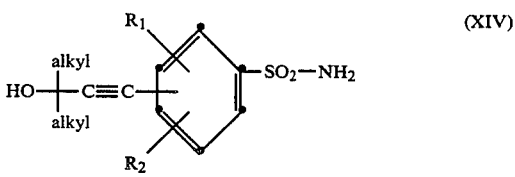

under the above conditions, with the aromatic halide of the formula XI, in which formulae above R$_1$ and R$_2$ are as defined for formula I, Hal is bromine or iodine and alkyl is a C$_1$-C$_4$alkyl radical.

The compounds of formula II employed as intermediates are novel and have been specially developed for the synthesis of compounds of formula I. These intermediates constitute a further object of the invention.

The phenylsulfonylisocyanates of the formula IV can be obtained by reacting the phenylsulfonamides of the formula II with phosgene, in the presence of butylisocyanate, in a chlorinated hydrocarbon as solvent, at reflux temperature. Similar reactions are described in "Newer Methods of Preparative Organic Chemistry", Vol. VI, 223–241, Academic Press, New York and London.

The isothiocyanates of the formula IV are obtained by treating the phenylsulfonamides of formula II with carbon disulfide and potassium hydroxide and by subsequent reaction of the dipotassium salt with phosgene. Such processes are described in Arch. Pharm. 299, 174 (1966).

The N-phenylsulfonylcarbamates of the formula VII are obtained by reacting the phenylsulfonamides of the formula II with diphenyl carbonate in the presence of a base. Similar processes are described in Japanese patent specification No. 61 169.

The starting materials of the formulae III, V and VI are known or they can be prepared by known methods.

Isocyanates of the formula VI can be prepared by reacting amines of the formula V with oxalyl chloride in a chlorinated hydrocarbon as solvent. Amines of the formula V are known and some are commercially available, or they can be prepared by known methods, q.v. "The Chemistry of Heterocyclic Compounds", Vol. XIV, Interscience Publishers, New York, London.

It is convenient to carry out these reactions for obtaining compounds of formula I in aprotic, inert organic solvents such as methylene chloride, tetrahydrofuran, acetonitrile, dioxan or toluene.

The reaction temperatures are preferably in the range from $-20°$ to $+120°$ C. The reactions are normally slightly exothermic and can be carried out at room temperature. To shorten the reaction time or also to initiate the reaction it is expedient to heat the reaction mixture briefly to boiling point. The reaction times can also be shortened by addition of a few drops of a base or isocyanate as catalyst.

The final products can be isolated by concentrating the reaction mixture and/or removing the solvent by evaporation, and by recrystallisation or by triturating the solid residue in a solvent in which it is poorly soluble, such as an ether, an aromatic hydrocarbon or a chlorinated hydrocarbon.

The compounds of formula I are stable compounds, and no protective measures are required for handling them.

When used in low rates of application, the compounds of formula I have good selective growth inhibiting and selective herbicidal properties which make them most suitable for use in crops of useful plants, especially in cereals, cotton, soybeans, maize and rice. In some cases damage is also caused to weeds which have only been controlled up to now with total herbicides.

The mode of action of some of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of the formula I are effective even when used in very low rates of application.

The compounds of formula I have pronounced growth-regulating, especially growth-inhibiting, properties. The growth of both monocots and dicots is inhibited. Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Further, the compounds of formula I are suitable for preventing stored potatoes from seeding. During winter storage, potatoes often develop sprouts which result in shrinkage, weight loss, and rot.

At higher rates of application, all tested plants are so severely damaged in their development that they die.

The invention also relates to herbicidal and growth-regulating compositions which contain a novel compound of the formula I, and also to methods of controlling weeds pre- and postemergence and of inhibiting the growth of monocots and dicots, especially grasses, tropical cover crops and tobacco plant suckers.

The compounds of the formula I are used in unmodified form, or preferably, together with the adjuvants conventionally employed in the art of formulation, and are therefore, formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having goot emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethylanolamine salts of naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipides.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ridgewood, N.J., 1979, and Sisley and Wood, "Encyclopedia of Surface Active Agents", Chemical Publishing Co., Inc. New York, 1964.

The pesticidal compositions usually contain 0.1 to 95%, preferably 0.1 to 80%, of a compound of the formula I, 1 to 99.9%, of a solid or liquid adjuvant, and 0 to 25%, preferably 0.1 to 25%, of a surfactant.

Preferred formulations are composed in particular of the following constituents (%=percentage by weight):

| Emulsifiable concentrates | | |
|---|---|---|
| active ingredient: | 10 to 20%, | preferably 5 to 10% |
| surfactant: | 5 to 30%, | preferably 10 to 20% |
| liquid carrier: | 20 to 94%, | preferably 70 to 85% |
| Dusts | | |
| active ingredient: | 0.1 to 10%, | preferably 0.1 to 1% |
| solid carrier: | 99.9 to 90%, | preferably 99.9 to 99% |
| Suspension concentrates | | |
| active ingredient: | 5 to 75%, | preferably 10 to 50% |
| water: | 94 to 25%, | preferably 90 to 30% |
| surfactant: | 1 to 40%, | preferably 2 to 30% |
| Wettable powders | | |
| active ingredient: | 0.5 to 90%, | preferably 10 to 80% |
| surfactant: | 0.5 to 20%, | preferably 1 to 15% |
| solid carrier: | 5 to 95%, | preferably 15 to 90% |
| Granulates | | |
| active ingredient: | 0.5 to 30%, | preferably 3 to 15% |
| solid carrier: | 99.5 to 70%, | preferably 97 to 85%. |

Whereas commerical products will be preferably formulated as concentrates, the end user will normally employ dilute formulations. The formulations can be diluted to a concentration as low as 0.001%. The rates of application are normally from 0.01 to 10 kg a.i./ha, preferably from 0.025 to 5 kg a.i./ha.

The compositions may also contain further ingredients, such as stabilisers, antifoams, viscosity regulators, binders, tackifiers as well as fertilisers or other active ingredients in order to obtain special effects.

PREPARATORY EXAMPLES

Example 1

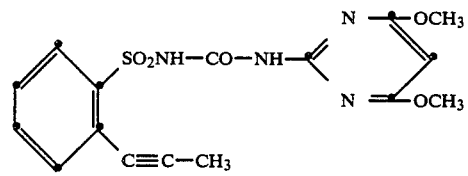

N-[2-(propyn-1-yl)phenylsulfonyl]-N'-(4,6-dimethoxypyrimidin-2-yl)urea (compound 5.1)

(a) 2-(propyn-1-yl)phenylsulfonamide:

To a solution of 28.3 g (0.1 mole) of 2-iodophenylsulfonamide in 350 ml of dimethylformamide and 100 ml of triethylamine are added 1.0 g of palladium dichlorobis(triphenylphosphite) complex, $PdCl_2[P(C_6H_5)_3]_2$, and 0.5 g of copper(I) iodide (CuI). Gaseous propine is then introduced into this solution until the starting material is completely reacted. The reaction mixture is filtered and the residue is concentrated in vacuo and then taken up in water. The precipitate is isolated and dried. Recrystallisation from ethyl acetate/hexane yields 15.6 g (80%) of 2-(propyn-1-yl)phenylsulfonamide with a melting point of 147°–149° C.

(b) N-[2-(propyn-1-yl)phenylsulfonyl]-N'-4,6-dimethoxypyrimidin-2-yl)urea:

To a solution of 1.95 g (0.01 mole) of 2-(propyn-1-yl)phenylsulfonamide and 1.7 g of 1,8-diazabicyclo[5.4.0]-undec-7-ene in 33 ml of absolute dioxan are added, in portions, 2.75 g (1.01 mole) of 4,6-dimethoxy-2-phenoxycarbonylaminopyridine at 20°–25° C. over 30 minutes. The reaction mixture is subsequently stirred for 4 hours at 20°–25° C. and then taken up in a mixture of 66 ml of ice-water, 10 ml of 2N hydrochloric acid and 150 ml of ethyl acetate. The organic phase is separated and the aqueous phase is extracted with 66 ml of ethyl acetate. The combined organic extracts are washed with water and a saturated solution of sodium chloride, dried over magnesium sulfate and concentrated. The crystalline residue is washed with diethyl ether, affording 2.4 g (74%) of N-[2-(propyn-1-yl)phenylsulfonyl]-N'-4,6-dimethoxypyrimidin-2-yl)urea with a melting point of 193°–194° C.

The intermediates and final products listed in the subsequent tables are obtained in corresponding manner.

TABLE 1

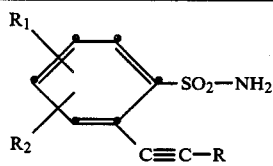

| No. | R | $R_2$ | $R_1$ | m.p. [°C.] |
|---|---|---|---|---|
| 1.1 | $CH_3$ | H | H | 147–149 |
| 1.2 | H | H | H | |
| 1.3 | $-C(CH_3)_2-OH$ | H | H | 200–201 |
| 1.4 | $C_6H_5$ | H | H | 85–88 |
| 1.5 | $4-Cl-C_6H_4-$ | H | H | |
| 1.6 | 2-thienyl | H | H | |
| 1.7 | 2-furyl | H | H | |
| 1.8 | 2-pyridyl | H | H | |
| 1.9 | $CH_3$ | 5-F | H | |
| 1.10 | H | 5-F | H | |
| 1.11 | $-C(CH_3)_2-OH$ | 5-F | H | |
| 1.12 | $C_6H_5$ | 5-F | H | |
| 1.13 | 2-thienyl | 5-F | H | |
| 1.14 | 2-furyl | 5-F | H | |
| 1.15 | $CH_3$ | 6-Cl | H | |
| 1.16 | $CH_3$ | 6-$COOCH_3$ | H | |
| 1.17 | $CH_3$ | 6-$OCH_3$ | H | |
| 1.18 | $CH_3$ | 6-$OCHF_2$ | H | |
| 1.19 | $CH_3$ | 6-$CF_3$ | H | |
| 1.20 | $CH_3$ | 6-$CH_3$ | H | |

TABLE 2

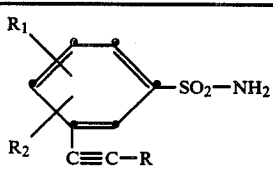

| No. | R | $R_2$ | $R_1$ | m.p. [°C.] |
|---|---|---|---|---|
| 2.1 | $CH_3$ | 6-Cl | H | |
| 2.2 | H | 6-Cl | H | |
| 2.3 | $-C(CH_3)_2-OH$ | 6-Cl | H | |

TABLE 2-continued

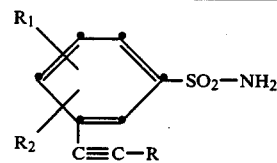

| No. | R | $R_2$ | $R_1$ | m.p. [°C.] |
|---|---|---|---|---|
| 2.4 | $C_6H_5$ | 6-Cl | H | |
| 2.5 | $CH_3$ | 6-F | H | |
| 2.6 | H | 6-F | H | |
| 2.7 | $-C(CH_3)_2-OH$ | 6-F | H | |
| 2.8 | $C_6H_5$ | 6-F | H | |
| 2.9 | $CH_3$ | H | H | |
| 2.10 | H | H | H | |
| 2.11 | $CH_3$ | 6-$COOCH_3$ | H | |
| 2.12 | $CH_3$ | 6-$CF_3$ | H | |
| 2.13 | $CH_3$ | 6-$OCH_3$ | H | |
| 2.14 | $CH_3$ | 6-$OCHF_2$ | H | |
| 2.15 | $CH_3$ | 6-$CH_3$ | H | |

TABLE 3

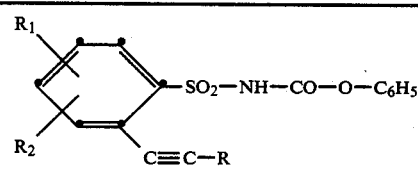

| No. | R | $R_2$ | $R_1$ | m.p. [°C.] |
|---|---|---|---|---|
| 3.1 | $CH_3$ | H | H | |
| 3.2 | H | H | H | |
| 3.3 | $-C(CH_3)_2-OH$ | H | H | |
| 3.4 | $C_6H_5$ | H | H | |
| 3.5 | $4-Cl-C_6H_4-$ | H | H | |
| 3.6 | 2-thienyl | H | H | |
| 3.7 | 2-furyl | H | H | |
| 3.8 | 2-pyridyl | H | H | |
| 3.9 | $CH_3$ | 5-F | H | |
| 3.10 | H | 5-F | H | |
| 3.11 | $-C(CH_3)_2-OH$ | 5-F | H | |
| 3.12 | $C_6H_5$ | 5-F | H | |
| 3.13 | 2-thienyl | 5-F | H | |
| 3.14 | 2-furyl | 5-F | H | |

TABLE 4

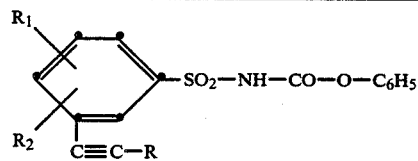

| No. | R | $R_2$ | $R_1$ | m.p. [°C.] |
|---|---|---|---|---|
| 4.1 | $CH_3$ | 6-Cl | H | |
| 4.2 | H | 6-Cl | H | |
| 4.3 | $-C(CH_3)_2-OH$ | 6-Cl | H | |
| 4.4 | $C_6H_5$ | 6-Cl | H | |
| 4.5 | $CH_3$ | 6-F | H | |
| 4.6 | H | 6-F | H | |
| 4.7 | $-C(CH_3)_2-OH$ | 6-F | H | |
| 4.8 | $C_6H_5$ | 6-F | H | |

TABLE 5

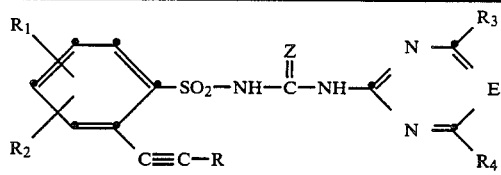

| No. | R | R₂ | R₁ | R₃ | R₄ | E | Z | m.p. [°C.] |
|---|---|---|---|---|---|---|---|---|
| 5.1 | CH₃ | H | H | OCH₃ | OCH₃ | CH | O | 193–194 |
| 5.2 | CH₃ | H | H | CH₃ | CH₃ | CH | O | 187–189 |
| 5.3 | CH₃ | H | H | CH₃ | OCH₃ | CH | O | 193 (decomp.) |
| 5.4 | CH₃ | H | H | OCH₃ | OCH₃ | N | O | |
| 5.5 | CH₃ | H | H | CH₃ | OCH₃ | N | O | 168–170 |
| 5.6 | CH₃ | H | H | OCH₃ | —N(CH₃)₂ | N | O | |
| 5.7 | CH₃ | H | H | CH₃ | —OCHF₂ | CH | O | |
| 5.8 | CH₃ | H | H | OCH₃ | —OCH₂—CF₃ | N | O | |
| 5.9 | H | H | H | OCH₃ | OCH₃ | CH | O | |
| 5.10 | H | H | H | CH₃ | CH₃ | CH | O | |
| 5.11 | H | H | H | CH₃ | OCH₃ | CH | O | |
| 5.12 | H | H | H | OCH₃ | OCH₃ | N | O | |
| 5.13 | H | H | H | CH₃ | OCH₃ | N | O | |
| 5.14 | H | H | H | OCH₃ | —N(CH₃)₂ | N | O | |
| 5.15 | H | H | H | CH₃ | —OCHF₂ | CH | O | |
| 5.16 | H | H | H | OCH₃ | —OCH₂—CF₃ | N | O | |
| 5.17 | C₆H₅ | H | H | OCH₃ | OCH₃ | CH | O | 166–169 |
| 5.18 | C₆H₅ | H | H | CH₃ | CH₃ | CH | O | |
| 5.19 | C₆H₅ | H | H | CH₃ | OCH₃ | CH | O | |
| 5.20 | C₆H₅ | H | H | OCH₃ | OCH₃ | N | O | |
| 5.21 | C₆H₅ | H | H | CH₃ | OCH₃ | N | O | |
| 5.22 | C₆H₅ | H | H | OCH₃ | —N(CH₃)₂ | N | O | |
| 5.23 | C₆H₅ | H | H | CH₃ | —OCHF₂ | CH | O | |
| 5.24 | C₆H₅ | H | H | OCH₃ | —OCH₂—CF₃ | N | O | |
| 5.25 | 4-Cl—C₆H₄— | H | H | OCH₃ | OCH₃ | CH | O | |
| 5.26 | 4-Cl—C₆H₄— | H | H | CH₃ | CH₃ | CH | O | |
| 5.27 | 4-Cl—C₆H₄— | H | H | CH₃ | OCH₃ | CH | O | |
| 5.28 | 4-Cl—C₆H₄— | H | H | OCH₃ | OCH₃ | N | O | |
| 5.29 | 4-Cl—C₆H₄ | H | H | CH₃ | OCH₃ | N | O | |
| 5.30 | 4-Cl—C₆H₄— | H | H | OCH₃ | —N(CH₃)₂ | N | O | |
| 5.31 | 4-Cl—C₆H₄— | H | H | CH₃ | —OCHF₂ | CH | O | |
| 5.32 | 4-Cl—C₆H₄— | H | H | OCH₃ | —OCH₂—CF₃ | N | O | |
| 5.33 | —C(CH₃)₂—OH | H | H | OCH₃ | OCH₃ | CH | O | 150 |
| 5.34 | —C(CH₃)₂—OH | H | H | CH₃ | CH₃ | CH | O | |
| 5.34 | —C(CH₃)₂—OH | H | H | CH₃ | OCH₃ | CH | O | |
| 5.36 | —C(CH₃)₂—OH | H | H | OCH₃ | OCH₃ | N | O | |
| 5.37 | —C(CH₃)₂—OH | H | H | CH₃ | OCH₃ | N | O | |
| 5.38 | —C(CH₃)₂—OH | H | H | OCH₃ | —N(CH₃)₂ | N | O | |
| 5.39 | —C(CH₃)₂—OH | H | H | CH₃ | —OCHF₂ | CH | O | |
| 5.40 | —C(CH₃)₂—OH | H | H | OCH₃ | —OCH₂—CF₃ | N | O | |
| 5.41 | C₂H₅ | H | H | OCH₃ | OCH₃ | CH | O | |
| 5.42 | C₂H₅ | H | H | CH₃ | CH₃ | CH | O | |
| 5.43 | C₂H₅ | H | H | CH₃ | OCH₃ | CH | O | |
| 5.44 | C₂H₅ | H | H | OCH₃ | OCH₃ | N | O | |
| 5.45 | C₂H₅ | H | H | CH₃ | OCH₃ | N | O | |
| 5.46 | C₂H₅ | H | H | OCH₃ | —N(CH₃)₂ | N | O | |
| 5.47 | C₂H₅ | H | H | CH₃ | —OCHF₂ | CH | O | |
| 5.48 | C₂H₅ | H | H | OCH₃ | —OCH₂—CF₃ | N | O | |
| 5.49 | 2-thienyl | H | H | OCH₃ | OCH₃ | CH | O | |
| 5.50 | 2-thienyl | H | H | CH₃ | CH₃ | CH | O | |
| 5.51 | 2-thienyl | H | H | CH₃ | OCH₃ | CH | O | |
| 5.52 | 2-thienyl | H | H | OCH₃ | OCH₃ | N | O | |
| 5.53 | 2-thienyl | H | H | CH₃ | OCH₃ | N | O | |
| 5.54 | 2-thienyl | H | H | OCH₃ | —N(CH₃)₂ | N | O | |
| 5.55 | 2-thienyl | H | H | CH₃ | —OCHF₂ | CH | O | |
| 5.56 | 2-thienyl | H | H | OCH₃ | —OCH₂—CF₃ | N | O | |
| 5.57 | 2-pyridyl | H | H | OCH₃ | OCH₃ | CH | O | |
| 5.58 | 2-pyridyl | H | H | CH₃ | CH₃ | CH | O | |
| 5.59 | 2-pyridyl | H | H | CH₃ | OCH₃ | CH | O | |
| 5.60 | 2-pyridyl | H | H | OCH₃ | OCH₃ | N | O | |
| 5.61 | 2-pyridyl | H | H | CH₃ | OCH₃ | N | O | |
| 5.62 | 2-pyridyl | H | H | OCH₃ | —N(CH₃)₂ | N | O | |
| 5.63 | 2-pyridyl | H | H | CH₃ | —OCHF₂ | CH | O | |
| 5.64 | 2-pyridyl | H | H | OCH₃ | —OCH₂—CF₃ | N | O | |
| 5.65 | CH₃ | H | H | Cl | OCH₃ | CH | O | |
| 5.66 | CH₃ | H | H | OCH₃ | —OCHF₂ | CH | O | |
| 5.67 | CH₃ | H | H | Cl | —OCHF₂ | CH | O | |
| 5.68 | CH₃ | H | H | —OCHF₂ | —OCHF₂ | CH | O | |
| 5.69 | CH₃ | H | H | OCH₃ | —N(CH₃)₂ | CH | O | |
| 5.70 | CH₃ | H | H | OCH₃ | CF₃ | CH | O | |
| 5.71 | CH₃ | H | H | OCH₃ | CH₂F | CH | O | |

TABLE 5-continued

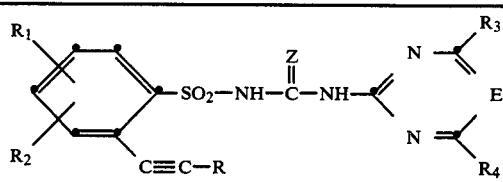

| No. | R | R₂ | R₁ | R₃ | R₄ | E | Z | m.p. [°C.] |
|---|---|---|---|---|---|---|---|---|
| 5.72 | CH₃ | H | H | OCH₃ | SCH₃ | CH | O | |
| 5.73 | CH₃ | H | H | OCH₃ | —SCHF₂ | CH | O | |
| 5.74 | CH₃ | H | H | —OCHF₂ | —N(CH₃)₂ | CH | O | |
| 5.75 | CH₃ | H | H | OCH₃ | —NHCH₃ | N | O | |
| 5.76 | CH₂ | H | H | OCH₃ | C₂H₅ | N | O | |
| 5.77 | CH₃ | H | H | OCH₃ | —OCH₂—CH₂Cl | N | O | |
| 5.78 | CH₃ | H | H | CH₃ | —O(CH₂)₂—N(CH₃)₂ | N | O | |
| 5.79 | CH₃ | H | H | CH₃ | —O(CH₂)₂—N(C₂H₅)₂ | N | O | |
| 5.80 | CH₃ | H | H | OCH₃ | —O(CH₂)₂—N(CH₃)₂ | N | O | |
| 5.81 | CH₃ | H | H | OCH₃ | —O(CH₂)₂—N(C₂H₅)₂ | N | O | |
| 5.82 | CH₃ | H | H | CH₃ | —O(CH₂)₂—N(CH₃)₂ | CH | O | |
| 5.83 | CH₃ | H | H | CH₃ | —O(CH₂)₂—N(C₂H₅)₂ | CH | O | |
| 5.84 | CH₃ | H | H | OCH₃ | —O(CH₂)₂—N(CH₃)₂ | CH | O | |
| 5.85 | CH₃ | H | H | OCH₃ | —O(CH₂)₂—N(C₂H₅)₂ | CH | O | |
| 5.86 | H | H | H | Cl | OCH₃ | CH | O | |
| 5.87 | H | H | H | OCH₃ | —OCHF₂ | CH | O | |
| 5.88 | H | H | H | Cl | —OCHF₂ | CH | O | |
| 5.89 | H | H | H | —OCHF₂ | —OCHF₂ | CH | O | |
| 5.90 | H | H | H | OCH₃ | —N(CH₃)₂ | CH | O | |
| 5.91 | H | H | H | OCH₃ | CF₃ | CH | O | |
| 5.92 | H | H | H | OCH₃ | CH₂F | CH | O | |
| 5.93 | H | H | H | OCH₃ | SCH₃ | CH | O | |
| 5.94 | H | H | H | OCH₃ | —SCHF₂ | CH | O | |
| 5.95 | H | H | H | —OCHF₂ | —N(CH₃)₂ | CH | O | |
| 5.96 | H | H | H | OCH₃ | —NHCH₃ | N | O | |
| 5.97 | H | H | H | OCH₃ | C₂H₅ | N | O | |
| 5.98 | H | H | H | OCH₃ | —OCH₂—CH₂Cl | N | O | |
| 5.99 | H | H | H | CH₃ | OCH₃ | N | S | |
| 5.100 | H | H | H | CH₃ | OCH₃ | CH | S | |
| 5.101 | H | H | H | CH₃ | CH₃ | CH | S | |
| 5.102 | H | H | H | OCH₃ | —N(CH₃)₂ | N | S | |
| 5.103 | H | H | H | OCH₃ | OCH₃ | N | S | |
| 5.104 | CH₃ | 5-F | H | OCH₃ | OCH₃ | CH | O | |
| 5.105 | CH₃ | 5-F | H | CH₃ | CH₃ | CH | O | |
| 5.106 | CH₃ | 5-F | H | CH₃ | —OCHF₂ | CH | O | |
| 5.107 | CH₃ | 5-F | H | CH₃ | —OCH₃ | N | O | |
| 5.108 | CH₃ | 5-F | H | OCH₃ | —N(CH₃)₂ | N | O | |
| 5.109 | H | 5-F | H | OCH₃ | OCH₃ | CH | O | |
| 5.110 | H | 5-F | H | CH₃ | CH₃ | CH | O | |
| 5.111 | H | 5-F | H | CH₃ | —OCHF₂ | CH | O | |
| 5.112 | H | 5-F | H | CH₃ | OCH₃ | N | O | |
| 5.113 | H | 5-F | H | OCH₃ | —N(CH₃)₂ | N | O | |
| 5.114 | H | 5-F | H | OCH₃ | CH₃ | CH | O | |
| 5.115 | —C(CH₃)₂—OH | 5-F | H | OCH₃ | OCH₃ | CH | O | |
| 5.116 | —C(CH₃)₂—OH | 5-F | H | OCH₃ | CH | CH | O | |
| 5.117 | —C(CH₃)₂—OH | 5-F | H | CH₃ | CH₃ | CH | O | |
| 5.118 | —C(CH₃)₂—OH | 5-F | H | CH₃ | —OCHF₂ | CH | O | |
| 5.119 | —C(CH₃)₂—OH | 5-F | H | CH₃ | —OCH₃ | N | O | |
| 5.120 | —C(CH₃)₃—OH | 5-F | H | OCH₃ | —N(CH₃)₂ | N | O | |
| 5.121 | —C(CH₃)₂—OH | 5-F | H | OCH₃ | OCH₃ | N | O | |
| 5.122 | C₂H₅ | 5-F | H | OCH₃ | OCH₃ | CH | O | |
| 5.123 | C₂H₅ | 5-F | H | CH₃ | OCH₃ | N | O | |
| 5.124 | C₆H₆ | 5-F | H | OCH₃ | OCH₃ | N | O | |
| 5.125 | C₆H₅ | 5-F | H | OCH₃ | —N(CH₃)₂ | N | O | |
| 5.126 | 2-thienyl | 5-F | H | OCH₃ | OCH₃ | CH | O | |
| 5.127 | 2-thienyl | 5-F | H | OCH₃ | CH₃ | N | O | |
| 5.128 | 2-furyl | 5-F | H | OCH₃ | OCH₃ | CH | O | |
| 5.129 | 2-furyl | 5-F | H | CH₃ | OCH₃ | N | O | |
| 5.130 | CH₃ | 6-Cl | H | OCH₃ | OCH₃ | CH | O | |
| 5.131 | CH₃ | 6-Cl | H | CH₃ | CH₃ | CH | O | |
| 5.132 | CH₃ | 6-Cl | H | CH₃ | OCH₃ | CH | O | |
| 5.133 | CH₃ | 6-Cl | H | OCH₃ | OCHF₂ | CH | O | |
| 5.134 | CH₃ | 6-Cl | H | OCH₃ | OCH₃ | N | O | |
| 5.135 | CH₃ | 6-Cl | H | CH₃ | OCH₃ | N | O | |
| 5.136 | CH₃ | 6-COOCH₃ | H | CH₃ | OCH₃ | N | O | |
| 5.137 | CH₃ | 6-COOCH₃ | H | CH₃ | OCH₃ | CH | O | |
| 5.138 | CH₃ | 6-OCH₃ | H | CH₃ | OCH₃ | N | O | |
| 5.139 | CH₃ | 6-OCH₃ | H | CH₃ | OCH₃ | CH | O | |
| 5.140 | CH₃ | 6-OCHF₂ | H | CH₃ | OCH₃ | N | O | |
| 5.141 | CH₃ | 6-OCHF₂ | H | CH₃ | OCH₃ | CH | O | |
| 5.142 | CH₃ | 6-CF₃ | H | CH₃ | OCH₃ | N | O | |
| 5.143 | CH₃ | 6-CF₃ | H | CH₃ | OCH₃ | CH | O | |

TABLE 5-continued

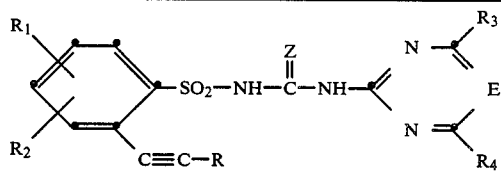

| No. | R | $R_2$ | $R_1$ | $R_3$ | $R_4$ | E | Z | m.p. [°C.] |
|---|---|---|---|---|---|---|---|---|
| 5.144 | H | 6-Cl | H | $CH_3$ | $OCH_3$ | N | O | |

TABLE 6

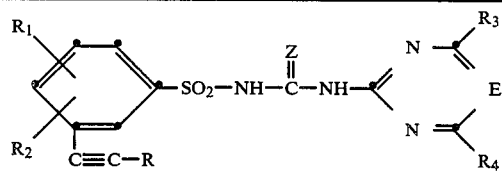

| No. | R | $R_2$ | $R_1$ | $R_3$ | $R_4$ | E | Z | m.p. [°C.] |
|---|---|---|---|---|---|---|---|---|
| 6.1 | $CH_3$ | 6-Cl | H | $CH_3$ | $-OCHF_2$ | CH | O | |
| 6.2 | $CH_3$ | 6-Cl | H | $CH_3$ | $OCH_3$ | N | O | |
| 6.3 | $CH_3$ | 6-Cl | H | $OCH_3$ | $OCH_3$ | CH | O | |
| 6.4 | H | 6-Cl | H | $CH_3$ | $-OCHF_2$ | CH | O | |
| 6.5 | H | 6-Cl | H | $CH_3$ | $OCH_3$ | N | O | |
| 6.6 | H | 6-Cl | H | $OCH_3$ | $OCH_3$ | CH | O | |
| 6.7 | $-C(CH_3)_2-OH$ | 6-Cl | H | $OCH_3$ | $OCH_3$ | CH | O | |
| 6.8 | $C_6H_5$ | 6-Cl | H | $OCH_3$ | $OCH_3$ | CH | O | |
| 6.9 | $CH_3$ | 6-F | H | $OCH_3$ | $OCH_3$ | CH | O | |
| 6.10 | $CH_3$ | 6-F | H | $CH_3$ | $CH_3$ | CH | O | |
| 6.11 | $CH_3$ | 6-F | H | $CH_3$ | $-OCHF_2$ | CH | O | |
| 6.12 | $CH_3$ | 6-F | H | $CH_3$ | $CH_3$ | N | O | |
| 6.13 | $CH_3$ | 6-F | H | $OCH_3$ | $-N(CH_3)_2$ | N | O | |
| 6.14 | H | 6-F | H | $OCH_3$ | $OCH_3$ | CH | O | |
| 6.15 | H | 6-F | H | $CH_3$ | $CH_3$ | CH | O | |
| 6.16 | H | 6-F | H | $CH_3$ | $-OCHF_2$ | CH | O | |
| 6.17 | H | 6-F | H | $CH_3$ | $OCH_3$ | N | O | |
| 6.18 | H | 6-F | H | $OCH_3$ | $-N(CH_3)_2$ | N | O | |
| 6.19 | H | 6-F | H | $OCH_3$ | $CH_3$ | CH | O | |
| 6.20 | $-C(CH_3)_2-OH$ | 6-F | H | $OCH_3$ | $OCH_3$ | CH | O | |
| 6.21 | $-C(CH_3)_2-OH$ | 6-F | H | $OCH_3$ | $CH_3$ | CH | O | |
| 6.22 | $-C(CH_3)_2-OH$ | 6-F | H | $CH_3$ | $CH_3$ | CH | O | |
| 6.23 | $-C(CH_3)_2-OH$ | 6-F | H | $CH_3$ | $-OCHF_2$ | CH | O | |
| 6.24 | $-C(CH_3)_2-OH$ | 6-F | H | $CH_3$ | $OCH_3$ | N | O | |
| 6.25 | $-C(CH_3)_2-OH$ | 6-F | H | $OCH_3$ | $-N(CH_3)_2$ | N | O | |
| 6.26 | $-C(CH_3)_2-OH$ | 6-F | H | $OCH_3$ | $OCH_3$ | N | O | |
| 6.27 | $C_6H_5$ | 6-F | H | $OCH_3$ | $OCH_3$ | CH | O | |
| 6.28 | $C_6H_5$ | 6-F | H | $CH_3$ | $OCH_3$ | N | O | |
| 6.29 | $C_6H_5$ | 6-F | H | $OCH_3$ | $OCH_3$ | N | O | |
| 6.30 | $C_6H_5$ | 6-F | H | $OCH_3$ | $-N(CH_3)_2$ | N | O | |
| 6.31 | 2-thienyl | 6-F | H | $OCH_3$ | $OCH_3$ | CH | O | |
| 6.32 | 2-thienyl | 6-F | H | $OCH_3$ | $OCH_3$ | N | O | |
| 6.33 | 2-furyl | 6-F | H | $OCH_3$ | $OCH_3$ | CH | O | |
| 6.34 | 2-furyl | 6-F | H | $OCH_3$ | $OCH_3$ | N | O | |
| 6.35 | $CH_3$ | H | H | $CH_3$ | $OCH_3$ | N | O | |
| 6.36 | $CH_3$ | H | H | $CH_3$ | $OCH_3$ | CH | O | |
| 6.37 | H | H | H | $CH_3$ | $OCH_3$ | CH | O | |
| 6.38 | $CH_3$ | 6-$COOCH_3$ | H | $CH_3$ | $OCH_3$ | CH | O | |
| 6.39 | $CH_3$ | 6-$COOCH_3$ | H | $CH_3$ | $OCH_3$ | N | O | |
| 6.40 | $CH_3$ | 6-$CF_3$ | H | $CH_3$ | $OCH_3$ | N | O | |
| 6.41 | $CH_3$ | 6-$CF_3$ | H | $CH_3$ | $OCH_3$ | CH | O | |
| 6.42 | $CH_3$ | 6-$OCH_3$ | H | $CH_3$ | $OCH_3$ | N | O | |
| 6.43 | $CH_3$ | 6-$OCH_3$ | H | $CH_3$ | $OCH_3$ | CH | O | |
| 6.44 | $CH_3$ | 6-$OCHF_2$ | H | $CH_3$ | $OCH_3$ | N | O | |
| 6.45 | $CH_3$ | 6-$OCHF_2$ | H | $CH_3$ | $OCH_3$ | CH | O | |
| 6.46 | $CH_3$ | 6-$CH_3$ | H | $CH_3$ | $OCH_3$ | N | O | |
| 6.47 | $CH_3$ | 6-$CH_3$ | H | $CH_3$ | $OCH_3$ | CH | O | |

Example 2

Formulation examples for compounds of formula I or mixtures thereof with herbicides (persentages are by weight)

| (a) Wettable powders | (a) | (b) | (c) |
|---|---|---|---|
| Compound of formula I | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicid acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| Compound of formula I | 10% | 1% |
| octylphenol polyethylene glycol ether (4–5 moles of ethylene oxide) | 3% | 3% |
| calcium dodecylbenzenesulfonate castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| Compound of formula I | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of formula I | 3% |
| polyethylene glycol 200 | 2% |
| kaolin | 94% |

The finely ground active ingredient is uniformly applied, in a mixer, to the kaolin moistened with polyethylene glycol. Non-dusty coated granulates are obtained in this manner.

| (f) silicone concentrate | (a) | (b) |
|---|---|---|
| Compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silocone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| Compound of formula I | 5% |
| isopropylamine | 1% |
| octylphenol polyethylene glycol ether (78 moles of ethylene oxide) | 3% |
| water | 91% |

BIOLOGICAL EXAMPLES

Example 3: Preemergence herbicidal action

Plastic pots are filled with expanded vermiculite (density: 0.135 g/cm$^3$, water-absorbing capacity: 0.565 l/l). After the non-adsorptive vermiculite has been saturated with an aqueous emsulion in deionised water which contains that test compound in concentration of 70.8 ppm, seeds of the following plants are sown on the surface: *Nasturtium officinalis, Agrostis tenuis, Stellaria media* and *Digitaria sanguinalis*. The pots are then kept in a climatic chamber at 20° C., an illumination of about 20 lux and a relative humidity of 70%. During the germinating phase of 4 to 5 days, the pots are covered with lightpermeable material and watered with deionised water to increase the local humidity. After the 5th day, 0.5% of a commercial liquid fertiliser (Greenzit ®) is added to the water. The test is evaluated 12 days after sowing and the action on the plants is assessed according to the following rating:

1: plants have not emerged or are totally withered
2–3: very pronounced action
4–6: medium action
7–8: weak action
9: no action (as untreated controls).

Preemergence action:
Concentration of the test compound emulsion: 70.8 ppm

| Test plant Compound | Nasturtium | Stellaria | Agrostis | Digitaria |
|---|---|---|---|---|
| 5.1 | 1 | 1 | 1 | 1 |
| 5.2 | 1 | 2 | 1 | 2 |
| 5.3 | 2 | 2 | 1 | 3 |
| 5.5 | 2 | 3 | 2 | 4 |
| 5.17 | 2 | 2 | 2 | 3 |
| 5.33 | 1 | 2 | 1 | 2 |

Example 4: Postemergence herbicidal action (contact action)

A number of weeds and cultivated plants, both monocots and dicots, are sprayed postemergence, in the 4- to 6-leaf stage, with an aqueous dispersion of test compound at a rate of application of 4 kg a.i./ha, and then kept at 24°-26° and 46-60% relative humidity. The test is evaluated 15 days after treatment using the same rating as in the preemergence test.

Postemergence action

| Compound | Avena | Solanum | Sinapis | Stellaria | Phaseolus |
|----------|-------|---------|---------|-----------|-----------|
| 5.1 | 6 | 2 | 2 | 4 | 2 |
| 5.33 | 6 | 2 | 3 | 5 | 3 |

Example 5: Inhibition of sprouting is stored potatoes

A number or commercially available potatoes of the "Urgenta" variety, without sprouts, are washed and dried. The potatoes are then immersed in emulsions of the compounds to be tested in different concentrations, placed on filter paper in plastic dishes, and kept in the dark at 14°-21° C. and 50% relative humidity. Evaluation is made 34 days after application.

The percentage weight loss of the tubers and the weight of the sprouts compared with untreated controls are simultaneously determined.

In the test, the compounds of the invention inhibit sprouting completely. At the same time, the weight loss of the potatoes is less than 10% of that of the controls.

Example 6: Growth inhibition of tropical cover crops

The test plants (centrosema plumieri and centrosema pubescens) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity.

In this test a marked reduction in new growth of the plants treated with compounds of the formula I is observed (less than 20% of the new growth of untreated control plants), without damage being caused to the test plants.

What is claimed is:

1. N-phenylsulfonyl-N'-triazinylurea of the formula

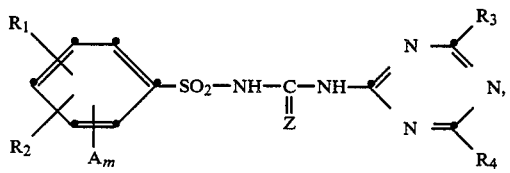

wherein

A is a radical of the formula $-C \equiv C - R$, m is 1 or 2,

Z is oxygen or sulfur,

R is hydrogen; branched or unbranched $C_1-C_9$alkyl which is unsubstituted or substituted by halogen, hydroxyl, $C_1-C_4$alkoxy, $C_1-C_4$alkylthio, $C_1-C_4$haloalkoxy, $C_3-C_9$cycloalkyl, cyano, $-COOR_6$, $-CONR_7R_8$ or by phenyl which is in turn unsubstituted or substituted by halogen, $C_1-C_4$alkyl, $C_1-C_4$alkoxy, nitro, cyano or trifluoromethyl; or is $C_3-C_9$cycloalkyl which is unsubstituted or substituted by halogen, hydroxyl, $C_1-C_4$alkyl, $C_1-C_4$alkoxy, $C_1-C_4$alkylthio, cyano, $-COOR_6$, $-CONR_7R_8$; or is phenyl or phenyl substituted by halogen, nitro, cyano, $C_1-C_4$alkyl, $C_1-C_4$alkoxy, $C_1-C_4$alkylthio, trifluoromethyl, $-COOR_6$ or $-CONR_7R_8$; or is a 5- or 6-membered heterocyclic ring selected from the group consisting of furan, thiophene, pyrrole, pyrazole, triazole, pyridine, pyrimidine, pyridazine, triazine, thiazole, oxazole, thiadiazole and oxadiazole, which is unsubstituted or substituted by halogen, $C_1-C_4$alkyl, $C_1-C_4$alkoxy, $-COOR_6$ or $-CONR_7R_8$, $R_1$ is hydrogen, halogen, $C_1-C_5$alkyl, $C_2-C_5$alkyl, $C_2-C_5$alkenyl or a radical $-Y-R_5$, $R_2$ is hydrogen, halogen, $C_1-C_5$alkyl, $C_2-C_5$alkenyl, $C_1-C_4$haloalkyl, or a radical $-Y-R_5$, $-COOR_6$, $-NO_2$ or $-CO-NR_7-R_8$, $R_3$ and $R_4$, each independently of the other, are hydrogen, $C_1-C_4$alkyl, $C_1-C_4$alkoxy, $C_1-C_4$alkylthio, $C_1-C_4$haloalkyl, $C_1-C_4$haloalkoxy, $C_1-C_4$haloalkylthio, halogen, $C_2-C_5$alkoxyalkyl, $-NR_9R_{10}$ or $-O-CH_2-CH_2-NR_9R_{10}$, $R_5$ and $R_6$, each independently of the other, are $C_1-C_5$alkyl, $C_2-C_5$alkenyl or $C_2-C_6$alkynyl, $C_1-C_5$haloalkyl, $C_2-C_5$haloalkenyl or $C_2-C_6$alkoxyalkyl, $R_7$ and $R_8$, each independently of the other, are hydrogen, $C_1-C_5$alkyl, $C_2-C_5$alkenyl or $C_2-C_6$alkynyl, $R_9$ is hydrogen, methyl or ethyl, $R_{10}$ is hydrogen, $C_1-C_4$alkyl, $C_1-C_4$alkoxy, methoxymethyl, cyanomethyl, cyanoethyl, $C_3-C_5$alkenyl or $C_3-C_6$alkynyl, and Y is oxygen, sulfur, a sulfinyl or sulfonyl bridge, or a salt thereof.

2. A compound according to claim 1, wherein Z is oxygen and m is 1, and $R_3$ and $R_4$ together contain not more than 4 carbon atoms.

3. A compound according to claim 2, wherein A is in the 2- or 3-position to the sulfonyl group, $R_1$ is hydrogen and $R_2$ is in the 5- or 6-position to the sulfonyl group.

4. A compound according to claim 3, wherein $R_2$ is hydrogen, chlorine, fluorine, nitro, trifluoromethyl, $C_1-C_4$haloalkoxy, $C_1-C_4$alkoxycarbonyl or $C_1-C_4$alkoxy, each of $R_3$ and $R_4$ is hydrogen, $C_1-C_4$alkyl, $C_1-C_4$alkoxy, $C_1-C_4$alkylthio, dialkylamino, $C_1-C_3$haloalkoxy, halogen or alkoxyalkyl, R is hydrogen or branched or unbranched $C_1-C_4$alkyl which is unsubstituted or substituted by halogen, hydroxyl, methoxy, methylthio, $C_1-C_4$haloalkoxy, cyclopropyl, cyano, methoxycarbonyl, or is phenyl, pyridyl, thienyl or furyl; and R is in the 2- or 3-position.

5. N-[2-(propyn-1-yl)-6-chlorophenylsulfonyl]-N'-(4-methoxy-6-methyl-1,3,5-triazin-2-yl)urea according to claim 1.

6. N[2-(propyn-1-yl)phenylsulfonyl]-N'-(4-methoxy-6-methyl-1,3,5-triazin-2-yl)urea according to claim 1.

7. A herbicidal and plant growth-inhibiting composition which contains at least one N-phenylsulfonyl-N'-triazinylurea according to claim 1, together with carriers and/or other adjuvants.

8. A method of controlling undesired plant growth which comprises applying to said plant growth a herbicidally effective amount of a N-phenylsulfonyl-N'-triazinylurea according to claim 1.

9. A method of inhibiting plant growth, which comprises applying to said plants a growth inhibiting effective amount of a N-phenylsulfonyl-N'-triazinylurea according to claim 1.

10. A method according to claim 8 for selectively controlling weeds pre- or postemergence in crops of useful plants.

11. A method according to claim 9 for inhibiting plant growth beyond the 2-leaf stage preemergence.

12. A method according to claim 9 for inhibiting the growth of leguminous cover crops.

13. A method according to claim 9 for inhibiting the sprouting of stored potatoes.

14. A method according to claim 10, wherein the crops of useful plants are cereals, cotton, soybeans, maize and rice.

* * * * *